US00PP27029P3

(12) United States Plant Patent
Musacchi et al.

(10) Patent No.: US PP27,029 P3
(45) Date of Patent: Aug. 9, 2016

(54) PEAR TREE NAMED 'PE1UNIBO'

(50) Latin Name: ***Pyrus communis* L.**
Varietal Denomination: PE1UNIBO

(71) Applicant: Alma Mater Studiorum—Università di Bologna, Bologna (IT)

(72) Inventors: Stefano Musacchi, Wenatchee, WA (US); Vincenzo Ancarani, Bologna (IT); Silviero Sansavini, Bologna (IT)

(73) Assignee: Alma Mater Studiorum—Università di Bologna, Bologna (IT)

( * ) Notice: Subject to any disclaimer, the term of this patent is extended or adjusted under 35 U.S.C. 154(b) by 97 days.

(21) Appl. No.: 14/121,606

(22) Filed: Sep. 24, 2014

(65) Prior Publication Data

US 2015/0327416 P1 Nov. 12, 2015

(30) Foreign Application Priority Data

May 9, 2014 (QZ) ..... PBR 2014/0969

(51) Int. Cl.
*A01H 5/08* (2006.01)

(52) U.S. Cl.
USPC ..... Plt./176

(58) Field of Classification Search
USPC ..... Plt./176
See application file for complete search history.

(56) References Cited

PUBLICATIONS

PLUTO Plant Variety Database Feb. 19, 2016. p. 1.*

* cited by examiner

*Primary Examiner* — Annette Para
(74) *Attorney, Agent, or Firm* — Foley & Lardner LLP

(57) ABSTRACT

The new and distinct *Pyrus communis* L. pear tree variety named 'PE1UNIBO' is particularly characterized by the following features: medium-high vigorous trees with upright growing habitus; bearing habitus normally on spurs on 2-3 years old branches; good grafting compatibility with the main quince rootstocks; early ripening (about 9 days before 'Bartlett'); high and constant yield and early bearing; green fruit, also when ripe, with slight russet (20-30%); fruit medium size with regular pyriform shape; tender and juicy white-cream flesh at full ripening stage with a very good flavor and high sugar content; possibility of eating the pear at the harvesting time, when crunchy; long storage capacity in cold room, up to 5-6 months.

5 Drawing Sheets

Latin name of the genus and species of the plant claimed: *Pyrus communis* L.

Variety denomination: 'PE1UNIBO'.

CROSS-REFERENCE TO RELATED APPLICATIONS

This application claims priority to European Community Plant Variety Office Plant Breeders' Rights Application No. 2014/0969 filed May 9, 2014.

BACKGROUND OF THE INVENTION

The present invention relates to a new and distinct variety of pear tree, botanically known as *Pyrus communis* L. of the Rosaceae family, and hereinafter referred to by the variety denomination 'PE1UNIBO'.

The new *Pyrus* variety is a product of a controlled breeding program conducted by the inventors, Stefano Musacchi, Silviero Sansavini and Vincenzo Ancarani, in Cadriano (Bologna), Italy. The variety is fully owned by Alma Mater Studiorum—Università di Bologna. The objective of the breeding program was to develop a new *Pyrus* variety with high and constant yield, early ripening, high fruit quality and long storability in cold room.

The new *Pyrus* variety originated from a cross made by the inventors in 1990 in Cadriano (Bologna), Italy. The female or seed parent is the *Pyrus communis* L. variety designated 'Abbé Fétel' (unpatented). The male or pollen parent is an unknown variety of *Pyrus communis* L. The new *Pyrus* variety was discovered and selected by the inventors within the progeny of the stated cross in a controlled environment in 1998 in Cadriano (Bologna), Italy.

Asexual reproduction of the new *Pyrus* variety by budding and grafting was first performed in August 1998 in Cadriano (Bologna), Italy, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'PE1UNIBO' which in combination distinguish this pear tree as a new and distinct variety:

1. Trees with medium-high vigor;
2. Good graft compatibility with the main quince rootstocks;
3. High and constant yield;
4. High quality fruit with good flavor;
5. High sugar content;
6. Green skin, also when ripe; and
7. Long storage capacity In comparison to the parental variety 'Abbé Fétel', the claimed variety differs primarily in the traits listed in Table 1.

TABLE 1

| Trait | New Variety 'PE1UNIBO' | Female Parent 'Abbé Fétel' |
|---|---|---|
| Compatibility with quince rootstock | Compatible | Partially |
| Fruit Shape | Pyriform; | Pyriform elongated (with the maximum diameter clearly toward calyx) |
| Skin color | Green with slightly russet | Yellow |
| Fruit size | Medium | Large |
| Harvest time | Early (9 days before 'Bartlett' pear) | Late (30 days after 'Bartlett' pear) |

Of the many commercial varieties known to the present inventors, the most similar in comparison to the new *Pyrus* variety 'PE1UNIBO' is the *Pyrus* variety 'Conference' (unpatented), in the following characteristics described in Table 2:

TABLE 2

| Characteristic | New Variety 'PE1UNIBO' | Comparison Variety 'Conference' |
|---|---|---|
| Growth habit | Upright | Upright, quite compact |
| Skin color | Green | Green |
| Fruit Shape | Pyriform | From pyriform to elongated pyriform |
| Size | Medium | Medium |
| Harvest time | Early | Medium-Late |

BRIEF DESCRIPTION OF THE DRAWINGS

The accompanying photographs illustrate the overall appearance of the new *Pyrus* variety 'PE1UNIBO' showing the colors as true as is reasonably possible with colored reproductions of this type. Colors in the photographs may differ slightly from the color values cited in the detailed botanical description, which accurately describe the color of 'PE1UNIBO'.

DETAILED BOTANICAL DESCRIPTION

Figure 1:
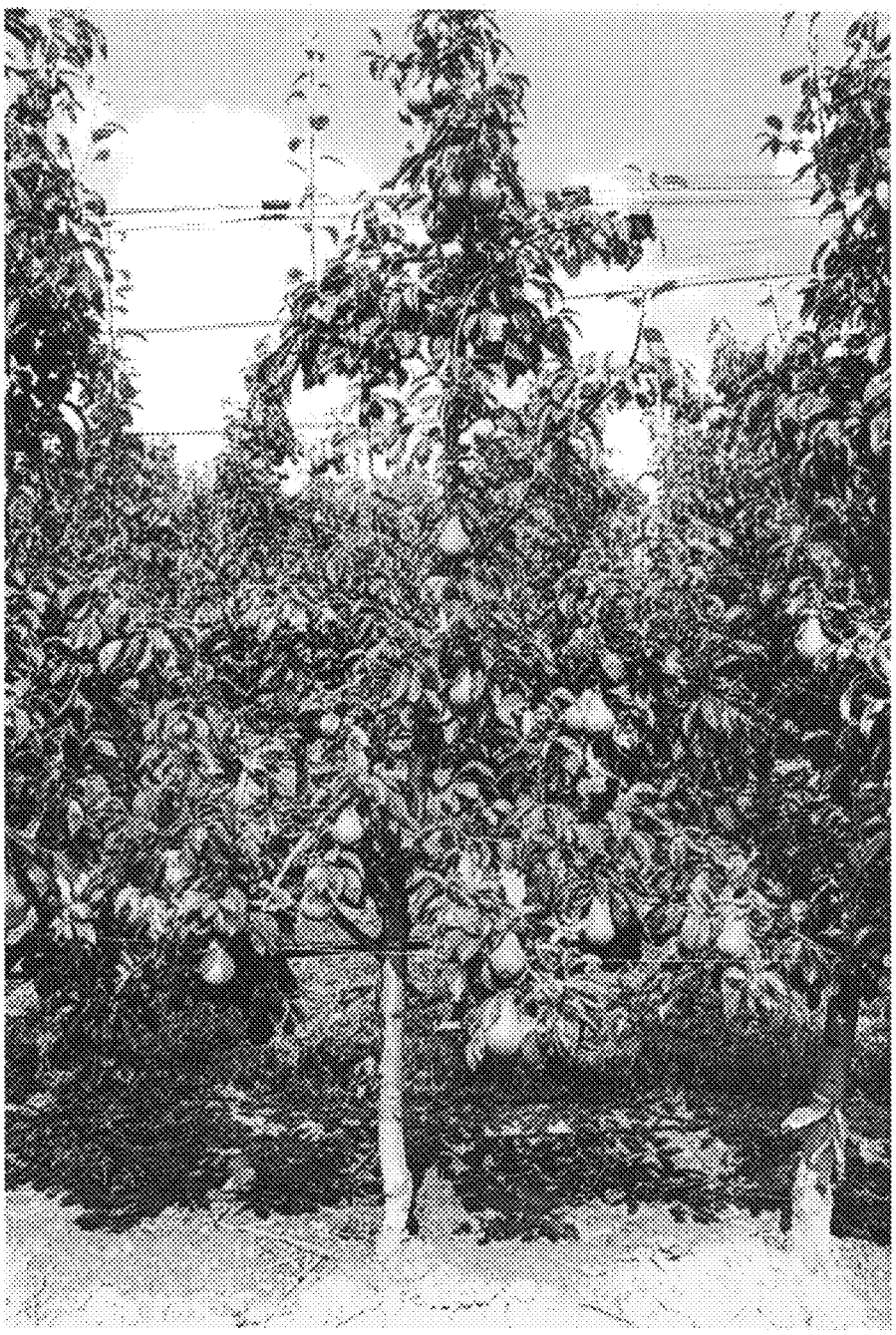
FIG. 1—shows a tree of 'PE1UNIBO' at seven years old.
Figure 2:
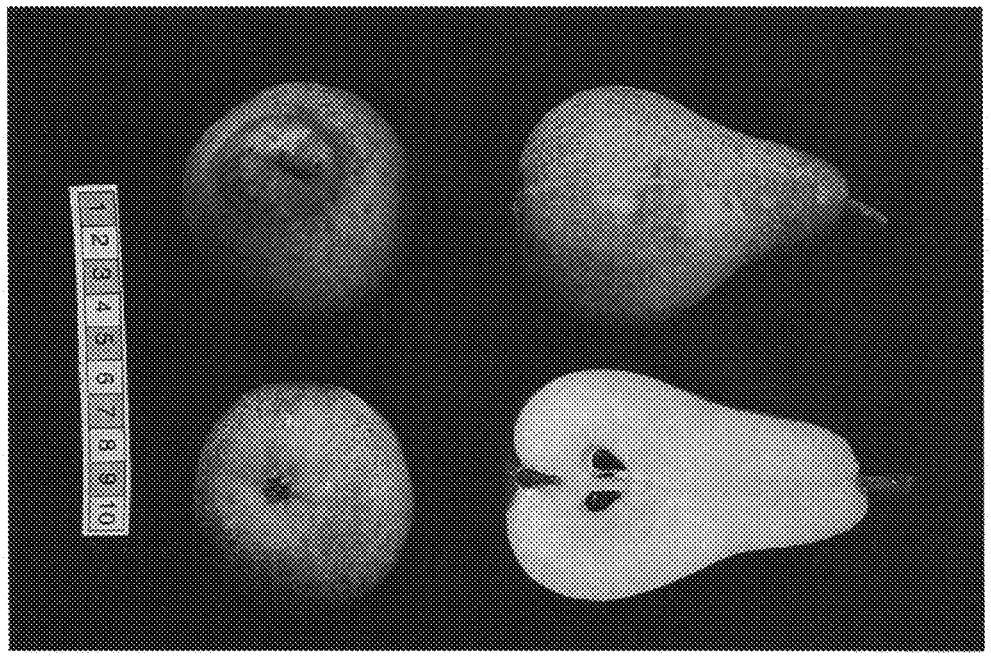
FIG. 2—shows typical fruits of 'PE1UNIBO'.
Figure 3:
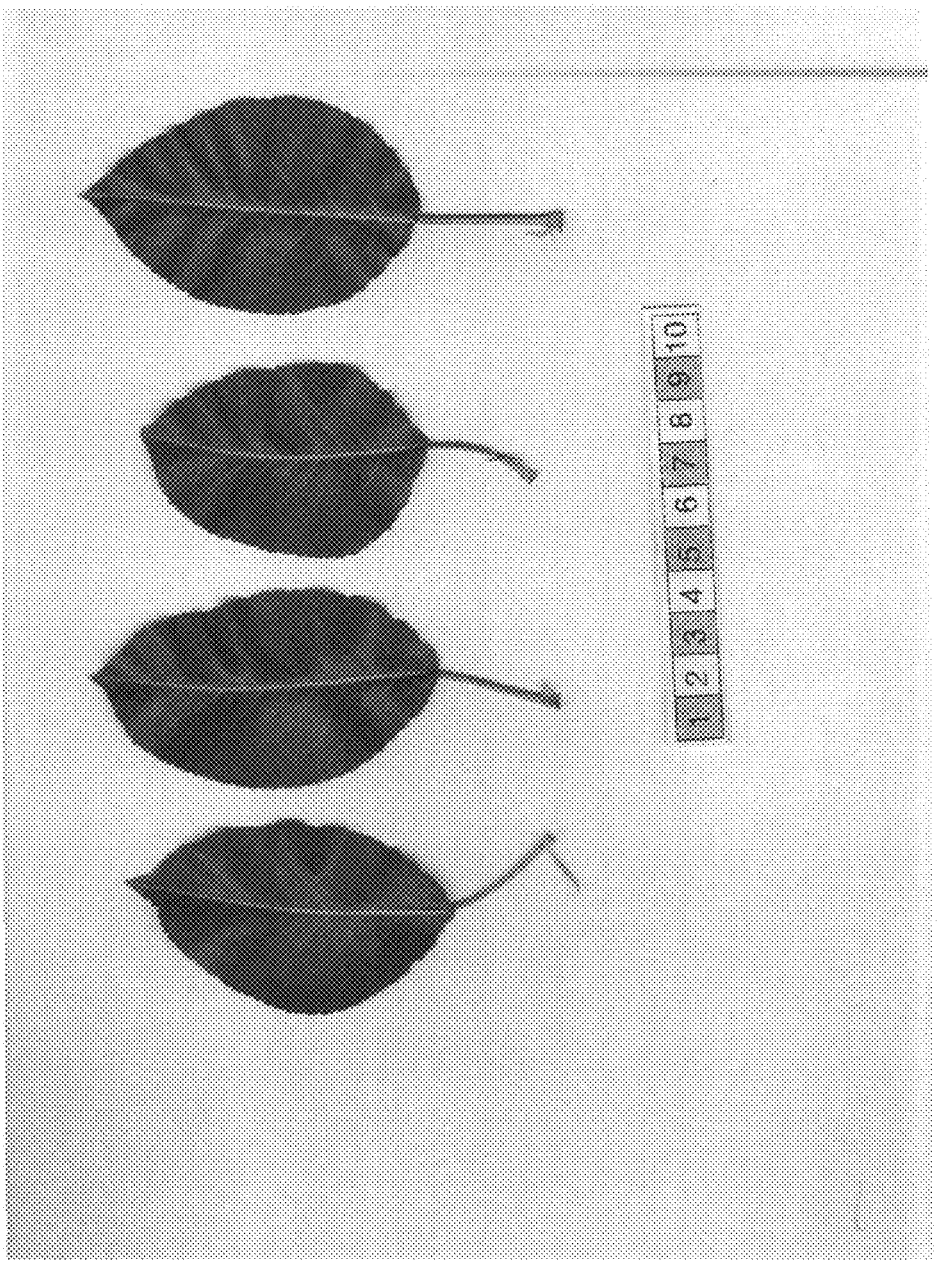
FIG. 3—shows the leafs of 'PE1UNIBO'.
Figure 4:
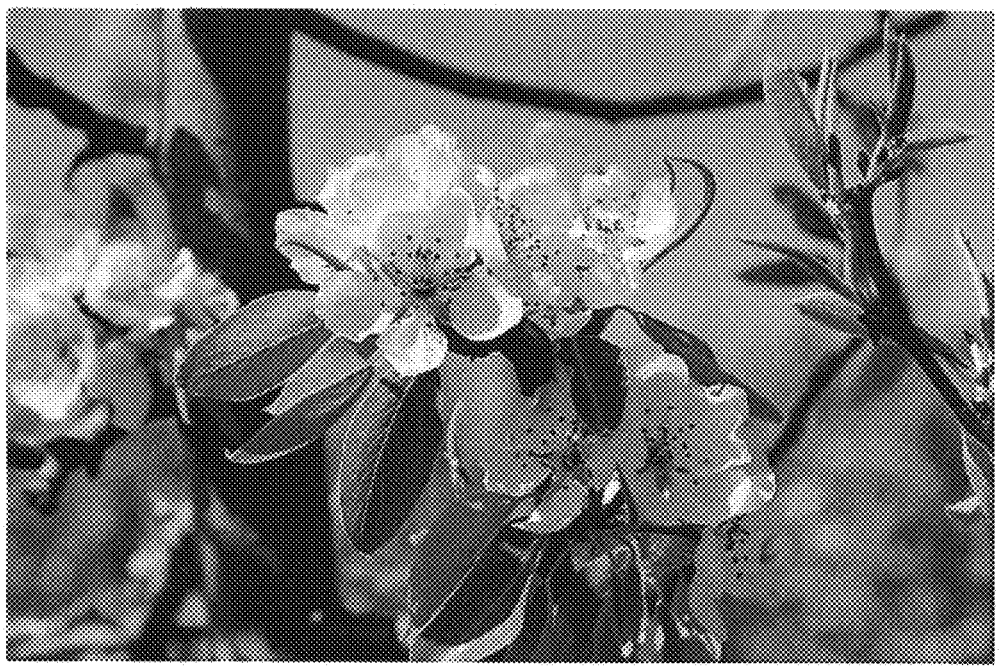
FIGS. 4 and 5—show different images of the flowers of 'PE1UNIBO', at full bloom.
Figure 5:
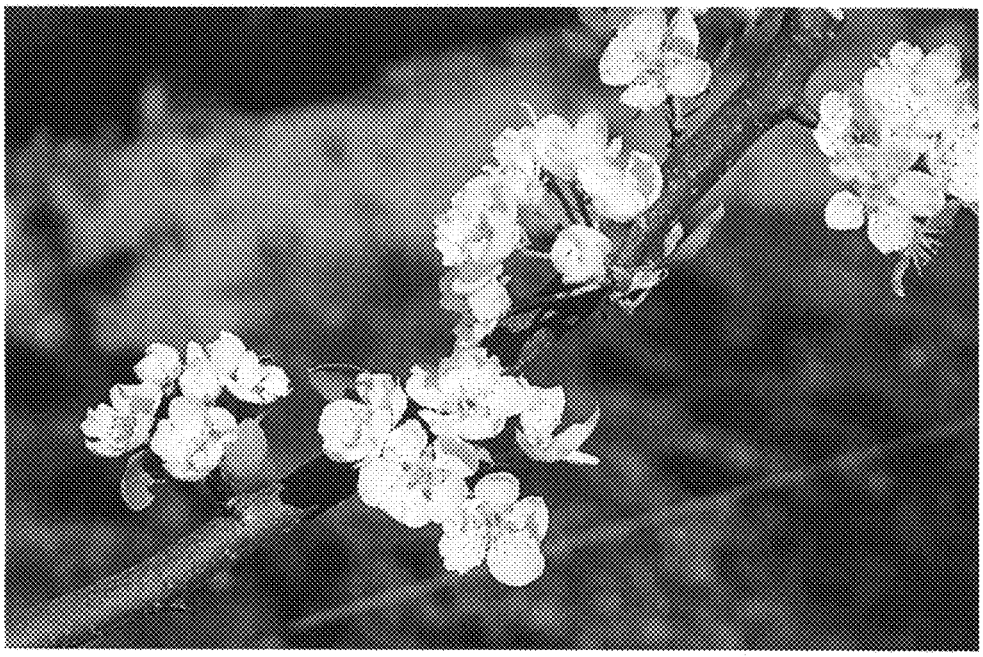

The new *Pyrus* variety 'PE1UNIBO' has not been observed under all possible environmental conditions. The phenotype of the new variety may vary with variations in environment such as temperature, light intensity, and day length without any change in the genotype of the pear tree.

The aforementioned photographs, together with the following observations, measurements and values describe trees of 'PE1UNIBO' as grown in the pear farm in Cadriano (Bologna), Italy, under conditions which closely approximate those generally used in commercial practice. The pear farm in which PE1UNIBO is growing has a clay soil; the climate is temperate continental with high summer temperatures and low winter temperatures; the orchard has a drip irrigation system used for fertigation.

Unless otherwise stated, the detailed botanical description includes observations, measurements and values based on 7 year old 'PE1UNIBO' trees grown in the pear farm in Cadriano (Bologna), Italy from 2008 to 2014. Quantified measurements are expressed as an average of measurements taken from a number of trees of 'PE1UNIBO'. The measurements of any individual tree or any group of trees, of the new variety may vary from the stated average.

Color references are made to The Royal Horticultural Society Colour Chart (R.H.S.), except where general colors of ordinary significance are used. Color values were taken under daylight conditions at approximately at 10:00 am in Cadriano (Bologna), Italy.

All of the trees of 'PE1UNIBO', insofar as they have been observed, have been identical in all the characteristics described below.

Classification:

*Botanical.*—*Pyrus communis* L.

*Commercial.*—*Pyrus* cv. PE1UNIBO.

Parentage:

*Female or seed parent.*—*Pyrus* variety designated 'Abbé Fétel' (unpatented).

*Male or pollen parent.*—Unknown.

Propagation: Budding and grafting.

Growing conditions:

*Light intensities.*—Full sunlight.

*Temperature* (*in the vegetative season, from March to September, measured in* 2013).—Minimum: 0.1° C. in March. Maximum: 38.9° C. in August. Medium: 8° C. (March) to 26.3° C. (July).

*Fertilization.*—A balanced fertilizer with level of N 80 kg/ha; $P_2O_5$ 50 kg/ha; $K_2O$ 120 kg/ha.

*Growth regulators.*—Not used.

*Pruning or trimming requirements.*—Winter pruning.

Tree:

*Age.*—Observed trees were seven years old and grafted on quince Rootstock Sydo®.

*Vigor.*—Medium-high vigor; early bearing; early abundant flowering; high and constant productivity; no biennial bearing. The variety is compatible with the main quince and pear rootstocks.

*Type of bearing.*—Typically on spurs on 2-3 years old branches (like 'Abbé Fétel').

*Form.*—Upright and conical: branches inserted with a narrow crotch angle. Form also depends on the training system used.

*Habit.*—A medium sized tree with one trunk and one leader; main branches spreading; symmetrical crown and rounded shape.

*Branching habit.*—Main branches angle is 20° to 60° with respect to trunk if allowed to grow naturally. The crotch angle changes along the trunk: the basal branches have a more right crotch angle whereas the upper and apical branches have a more narrow crotch angle.

*Density.*—Medium density.

*Size at maturity* (*depends on the training system*).—Height: About 3.1 m. Spread: About 1.4 m.

*Trunk.*—Height (up to leaders): About 2.7 m. Diameter: About 61 mm (measured 20 cm above the grafter point). Texture: At first, it is smooth with numerous and irregular lenticels (from rounded to elongated);

then the surface shows some grooves. Bark color: Primarily RHS 197D, with RHS 175C under bark. Trunk Lenticels (from rounded to elongated): Length: About 0.88 mm to 6.77 mm. Width: About 0.58 mm to 3.09 mm. Color: RHS 197A. Density: 1.6 n°/cm$^2$.

*Branches* (*on trees at year* 7).—Number per tree: About 15. Length: Varies due to pyramidal shape of tree; maximum of 90 cm to 130 cm; minimum of 10 cm to 30 cm. Diameter: About 12 mm to 32 mm. Surface texture: smooth with many lenticels. Pubescence: absent. Color: Mature (after about 3-4 years old): RHS 197A. New Growth: RHS 165B (sunny side); RHS 175C (shady side). Internode length (in the middle of branches): About 2 cm to 3.5 cm. Internode diameter (in the middle of branches): About 3.5 mm to 8 mm. Branch lenticels (from rounded to slightly elongated): Length: About 1.46 mm to 2.9 mm. Width: About 0.54 mm to 1.25 mm. Color: RHS 201A (sunny side); RHS 165B (shady side). Density: 1.3 n°/cm$^2$. One Year old Shoot lenticels (from rounded to ovate): Length: About 0.84 mm to 1.63 mm. Width: About 0.55 mm to 1.12 mm. Color: RHS 201A (sunny side); RHS 165B (shady side). Density: 3.1 n°/cm$^2$.

*Spur.*—Present: Yes. Distance between each spur: On the 3 years old branches, the distance is about 20 mm to 35 mm. Diameter of each spur: About 4.4 mm. Number of fruit per spur: About 2 to 4.

*Leaves*.—Arrangement: Alternate, simple and arranged upwards in relation to the shoot.

*Lamina.*—Size: Length: About 7.2 mm (from 5.2 mm to 9.1 mm fully expanded leaf). Width: About 4.0 mm (from 3 mm to 5.7 mm fully expanded leaf). Length/width ratio: 1.8. Overall Shape: the shape of leaf blade is "oval" with a medium-long pointed tip; the leaf area is medium: 26 cm$^2$; the longitudinal axis is medium curved. Base shape: right-angled. Apex shape: from right-angled to acute. Margin: moderately serrate with a medium depth of incisions of margin. Texture: Upper surface: glabrous. Under surface: glabrous. Pubescence: Upper surface: absent. Under surface: absent. Color (mature leaves): Upper surface: RHS 146A. Under surface: RHS 147C. Color (immature leaves): Upper surface: RHS 144A. Under surface: RHS 146D.

*Venation.*—Type: pinnate venation from central vein to the leaf edge. Color: RHS 152C.

*Petiole.*—Length: About 3.4 mm. Diameter: About 1.03 mm. Color: RHS 151A.

*Stipule.*—Arrangement: present in small numbers; the distance from basal attachment of petiole is short. Length (distance of stipules from basal attachment of petiole): About 1 mm to 3 mm. Width: About 3 mm to 12 mm.

Inflorescence:

*Blooming time.*—Full bloom around Mar. 30$^{th}$ in 2012 in Cadriano (Bologna), Italy.

*Blooming period.*—About 12 days, from March 26$^{th}$ to April 6$^{th}$.

*Fragrance.*—Not detected.

*Type.*—Corymb.

*Number of flowers per inflorescence.*—About 5 to 7.

*Inflorescence size.*—Diameter: About 4 cm. Depth: About 3.5 cm.

*Buds* (*vegetative bud on* 1 *year old shoot*).—Terminal Buds: Number per spur: About 1 to 2. Shape: acute apex; the bud support is slightly swollen. Length: About 8.3 mm. Width: About 4.1 mm. Color: Apex, RHS 200C, and base, RHS 200B. Texture: smooth; medium bud support. Pubescence: Absent. Lateral Buds: Number per spur: 1. Shape: acute apex; the position of vegetative bud in relation to shoot is slightly held out; the bud support has generally a medium-small size. Length: About 6.1 mm. Width: About 3.4 mm. Color: Apex, RHS 200C, and base, RHS 200B. Texture: smooth. Pubescence: Absent. Flower Buds (on 2-3 years old branches): Number per spur: 1. Shape: pointed. Length: About 7.5 mm. Width: About 3.5 mm. Color: Apex, RHS 200C, and base, RHS 200B. Texture: smooth. Pubescence: Absent.

*Petals.*—Number per flower: Five. Size: medium. Length: About 13 mm. Width: About 9 mm. Length/width ratio: 1.4. Overall shape: normally rounded; the margins of petals touch each other. Apex shape: rounded. Base shape: rounded. Texture (upper surface): smooth. Texture (lower surface): smooth. Margin: entire. Color (upper surface): White at full bloom. Color (lower surface): White at full bloom.

*Sepals.*—Number per flower: Five.

*Pollination requirements.*—Can be pollinated by several varieties of pear trees.

Fruit:

*Keeping quality.*—The fruit keeps well on the tree; The fruit can be stored in cold temperature conditions for up to 5-6 months without loss of firmness and juiciness. The shelf life ranges from one week to ten days without having a loss of firmness and juiciness. It's possible to eat the fruit also not totally ripe.

*Maturity when described.*—Ripe for eating.

*Maturity period after full bloom.*—About 125 days after full bloom, around July 30$^{th}$.

*Type.*—Pome.

*General shape.*—Normally pyriform, with the maximum diameter clearly towards the calyx; the fruit profile is concave. The stem is medium-short.

*Average weight.*—About 170 g.

*Fruit size.*—Average height: About 86.3 mm. Average diameter (at widest point): About 66.1 mm. Height/thickness ratio: 1.31.

*Stem.*—Length: About 20.2 mm. Diameter: About 4.2 mm. Color: RHS 199A.

*Basin.*—Depth: About 9.3 mm. Width: About 22.95 mm.

*Calyx.*—Depth: About 11.3 mm. Width: About 7.99 mm. Crowning at calyx end: weak. Calyx tube: Closed (it does not communicate with locules), but rather deep. At harvest the sepals are converging.

*Skin.*—Thickness: medium thin. Texture: smooth, with 20-30% of slight russet, predominantly localized at the top of the fruit and around the calyx. Color: RHS 144B (at picking time); 144C (when ripe). Lenticels: very small and round, point shape; not measured. Color: RHS 165B. Density: 43.5 n°/cm$^2$.

*Flesh.*—Firmness (at picking time): 5.5 to 6.3 kg (measured with an 8 mm tip). Color: RHS 150D. Texture: Fine, tender and juicy at full ripening time; with some veining in the flesh. The fruit can also be eaten not fully ripe. Aroma: aromatic; good flavor, sweet taste. Sugar content (at picking time): 14.5 to 16.6° Brix. Acidity/Starch (at picking time) 2.58 to 3.34 g/lt malic acid. Core: Symmetry of core: slightly symmetric. Distinctness of core lines: medium. Locules: Number (per fruit): 5. Length: About 15 mm. Width: About 10 mm. Form: the seed fills almost the locule cavity.

Seeds:

*Number per fruit.*—About 1 to 10.

*Number per locule.*—About 1 to 2.

*Shape.*—Ovate.

*Length.*—About 0.9 mm.

*Width.*—About 4 mm.

*Texture.*—Smooth.

*Color.*—RHS 165A.

Use: Fresh market.

Disease/pest resistance: Unknown; tests for tolerance to Fire Blight (*Erwinia amylovora*) in progress.

Disease/pest susceptibility: None observed.

Winter hardiness: No winter cold damage to wood and buds of dormant pear trees have been observed during the years of evaluation; but open flowers and young fruitlets are killed by exposure to −1.5 to −3° C., depending on the length of exposure.

Drought/heat tolerance: Tolerant to temperatures up to 38° C., growth is limited by drought periods without irrigation.

What is claimed is:

1. A new and distinct variety of *Pyrus communis* L. pear tree named 'PE1UNIBO', as illustrated and described herein.

* * * * *